United States Patent [19]

Mikkelsen

[11] Patent Number: Plant 5,962

[45] Date of Patent: Apr. 28, 1987

[54] KALANCHOE PLANT NAMED AVANTI

[75] Inventor: James C. Mikkelsen, Ashtabula, Ohio

[73] Assignee: Mikkelsens, Inc., Ohio

[21] Appl. No.: 782,457

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Avanti, characterized by its relatively large orange-red flowers and floriferous habit; small, dense foliage; compact growth habit with high degree of basal and side branching; early flowering, and its resistance to disease.

1 Drawing Figure

The present invention relates to a new and distinct cultivar of Kalanchoe plant, botanically known as *Kalanchoe blossfeldiana,* and known by the cultivar name Avanti. Avanti was developed by me through controlled breeding by crossing Mikkelsen seedling No. 82-477-7 (seed parent) with Mikkelsen seedling No. 82-399-1 (pollen parent). Neither parent is patented or commercial.

Asexual reproduction by stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Avanti is particularly characterized by its bright red flowers, compact growth habit, high degree of basal branching, and early flowering.

2. Basal and side branching is equal to Attraction (Plant Patent applied for), and superior to Pollux (U.S. Plant Pat. No. 4,816) and Inspiration (Plant Patent applied for).

3. Avanti is darker red in color than Pollux and Attraction, and generally equal in color to Inspiration but brighter in appearance.

4. Overall flower size is equal to Pollux and Attraction but larger than Inspiration. However, individual petals are not as broad as Pollux and Attraction.

5. Avanti is similar in height to Pollux and Attraction, but more dwarf than Inspiration.

6. Leaf size is equal to Attraction but smaller than Inspiration and Pollux. Foliage is very dense.

7. Leaf margin is crenate like Inspiration but not as deeply lobed, while Pollux and Attraction have a more dentate leaf.

8. After flower initiation, plants must be treated with B-9 to reduce peduncle and pedicel elongation.

9. Highly floriferous, with larger flower head than Pollux, Attraction and Inspiration. In many cases, plant will flower from top of plant to rim of pot. The cultivar is outstanding for 10 cm pot production.

10. Avanti displays additional side branching on the basal branches which has not been observed on Pollux, Attraction and Inspiration.

The accompanying colored photograph, taken in August of 1985, illustrates in perspective view the overall appearance of Avanti, showing the colors as true as it is reasonably possible to obtain in a colored reproduction of this type.

The following is a detailed description of my new Kalanchoe cultivar based on plants produced under commercial practices in greenhouses in Ashtabula, Ohio. Color references are made to The Royal Horticultural Society Colour Chart (RHS) except where general terms of ordinary dictionary significance are used. It should be noted that precise color values could not be identified, with the values given below being as close as possible.

Parentage: A controlled cross between Mikkelsen seedling No. 82-477-7 and Mikkelsen seedling No. 82-399-1.

Propagation:

(A) *Type cutting.*—Stem cutting up to 2 cm long.

(B) *Time to root.*—10 days at 21° C. summer, 14 days at 21° C. winter.

(C) *Rooting habit.*—Many fine fibrous roots.

Plant description:

(A) *Form.*—Short, compact, upright; best suited for growing and scheduling practices for a 10 cm pot.

(B) *Habit of growth.*—Moderate rate of growth with branching from nearly every node; excellent basal branching with some compound basal branching; plant has a very dense appearance.

(C) *Foliage.*—Leaves simple, opposite. (1) Size: Average full grown leaf of flowering plant in a 10 cm pot is 105 mm long and 70 mm wide. (2) Shape: Ovate. (3) Texture: Glabrous, coriaceous, succulent. (4) Margin: Crenate. (5) Color: Young foliage, top side 137A; under side 137C. Mature foliage top side 147A, underside 147B.

Flowering description:

(A) *Flowering habits.*—Cyme inflorescence; each shoot is formed by dichotomous branching starting with the opening of the terminal flowers of the main axis, followed by terminal flowers of the side branches and continuing with subsequent development of branches in the inflorescence. Major inflorescence is 80 to 90 mm in diameter, and lateral inflorescences are 45 to 55 mm in diameter in a 10 cm pot.

(B) *Natural flowering season.*—Early January. Flowering time under controlled daylength at 20° C. in summer is 10 weeks; in winter is 12 weeks. Flowering time depends on temperature, light intensity, and other growing conditions.

(C) *Flower buds.*—Oblong up to 8 mm long, developing to tubular as flower petals mature, sheathed with four green sepals; corolla at maturity 12 mm long.

(D) *Flowers borne.*—Compound dichasial cymes; peduncle 3 mm in diameter, with peduncle length depending on growing conditions and Alar application; pedicels up to 10 mm long.

(E) *Quantity of flowers.*—Highly floriferous, the main axis having over 120 flowers and side branches over 60 flowers, with over 10 side branches in a 10 cm pot.

(F) *Petals.*—(1) Shape: Oval, top cuspidate. (2) Color: Top side when opening, 44A (closest value), fading to a bright shade of 44B (closest value); under side 43C. (3) Number of petals:

Four (4) united in corolla; petals are 5 mm in diameter; flower 15 mm in total diameter.

(G) *Reproductive organs.*—(1) Stamens: Eight (8) in number. (a) Anther shape: Flat elliptical, yellow in color. (b) Filament color: Light green. (c) Pollen color: Yellow. (2) Pistels (a) Stigma: Flat, greenish white when immature to white when mature. (b) Styles: Light green. (c) Ovaries: Four (4) in number, celled, size 6 mm, light green color.

Disease resistance: Highly resistant to mildew and no foliar yellow has been seen to date.

I claim:

1. A new and distinct cultivar of Kalanchoe plant named Avanti, as illustrated and described, and particularly characterized by its relatively large orange-red flowers and floriferous habit; small, dense foliage; compact growth habit with high degree of basal and side branching; early flowering, and its resistance to disease.

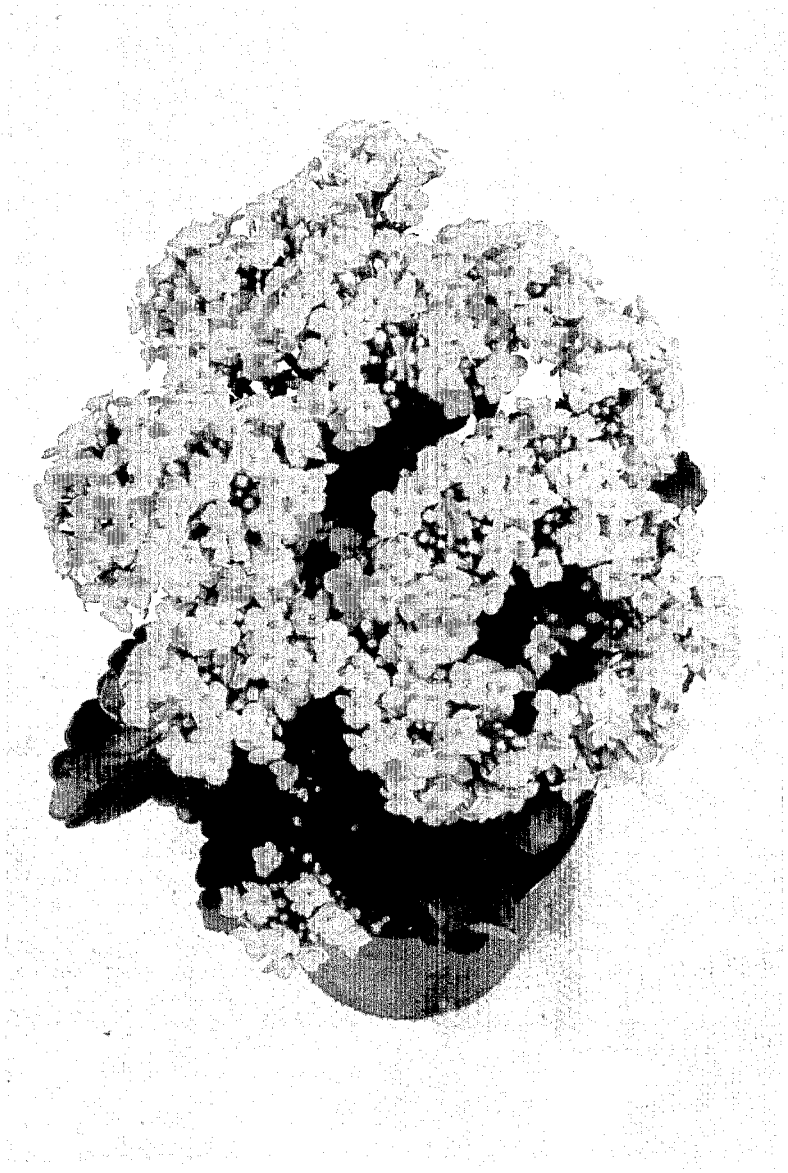

* * * * *